US00PP32796P2

(12) United States Plant Patent
Kerley et al.

(10) Patent No.: US PP32,796 P2
(45) Date of Patent: Feb. 2, 2021

(54) ***LAVANDULA* PLANT NAMED 'KERBEEPOWER'**

(50) Latin Name: *Lavandula angustifolia*
Varietal Denomination: KERBEEPOWER

(71) Applicants: Timothy Edward Kerley, Cambridge (GB); Sarah Elisabeth Kerley, Cambridge (GB); David William Kerley, Cambridge (GB); Priscilla Grace Kerley, Cambridge (GB)

(72) Inventors: Timothy Edward Kerley, Cambridge (GB); Sarah Elisabeth Kerley, Cambridge (GB); David William Kerley, Cambridge (GB); Priscilla Grace Kerley, Cambridge (GB)

( * ) Notice: Subject to any disclaimer, the term of this patent is extended or adjusted under 35 U.S.C. 154(b) by 0 days.

(21) Appl. No.: 16/602,898

(22) Filed: Dec. 19, 2019

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 6/502; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Lavandula angustifolia* plant named 'KERBEEPOWER' is disclosed, characterized by a compact, bushy plant, with short peduncles, and large flower spikes. Flowers are violet-blue. The new variety is a *Lavandula angustifolia*, suitable for outdoor landscape and container use.

4 Drawing Sheets

Latin name of the genus and species: *Lavandula angustifolia.*

Variety denomination: 'KERBEEPOWER'.

BACKGROUND OF THE INVENTION

The new cultivar is the product of a planned breeding program under the direction of the inventors, David Kerley, Priscilla Kerley, Sarah Kerley, and Timothy Kerley, all citizens of the United Kingdom. The objective of the breeding program was to produce new *Lavandula angustifolia* cultivars for commercial ornamental purposes. During the Summer of 2008, the inventors performed an open pollination of several unnamed, unpatented proprietary *Lavandula angustifolia* varieties with the seed parent *Lavandula angustifolia* 'Kerlavgem', U.S. Plant Pat. No. 23,001. This resulted in the selection of the new variety 'KERBEEPOWER' in July 2009. The breeding program and selection all took place at a commercial nursery in Cambridge, the United Kingdom.

Asexual reproduction of the new cultivar 'KERBEEPOWER' was first performed in Cambridge, UK in August 2009 by terminal vegetative cuttings and has shown that the unique features of this cultivar are stable and reproduced true to type in successive generations.

SUMMARY OF THE INVENTION

The cultivar 'KERBEEPOWER' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERBEEPOWER'. These characteristics in combination distinguish 'KERBEEPOWER' as a new and distinct *Lavandula* cultivar:

1. Compact, bushy plants.
2. Short peduncles.
3. Large flower spikes.
4. Violet-blue flowers.

PARENTAL COMPARISON

Plants of the new cultivar 'KERBEEPOWER' are similar to plants of seed parent in most horticultural characteristics, however, plants of the new cultivar differ in the following:

1. Plants of 'KERBEEPOWER' are much smaller and shorter than plants of 'KERLAVANGEM'.
2. Foliage of the new variety is wider than that of 'KERLAVANGEM'.
3. Flower color of the new variety is a different shade of violet-blue.

COMMERCIAL COMPARISON

Plants of the new cultivar 'KERBEEPOWER' are similar to plants of the unpatented variety *Lavandula angustifolia* 'Hidcote' in most horticultural characteristics, however, plants of the new cultivar 'KERBEEPOWER' differ in the following:

1. The new variety is a shorter plant than this comparator.
2. Flowers of the new variety are more violet-blue, while flowers of this comparator are violet.

Plants of the new cultivar 'KERBEEPOWER' are similar to plants of the unpatented variety *Lavandula angustifolia* 'BeeZee Dark Blue' in most horticultural characteristics, however, plants of the new cultivar 'KERBEEPOWER' differ in the following:

1. The new variety has 5 buds subtending from the bracts, while this comparator has 3.

BRIEF DESCRIPTION OF THE PHOTOGRAPHS

The accompanying photograph in FIG. 1 illustrates in full color a typical plant of 'KERBEEPOWER' grown outdoors in Cambridge, UK. The plant is approximately 1 year old shown in an approximately 10 inch pot.

Figure 1:
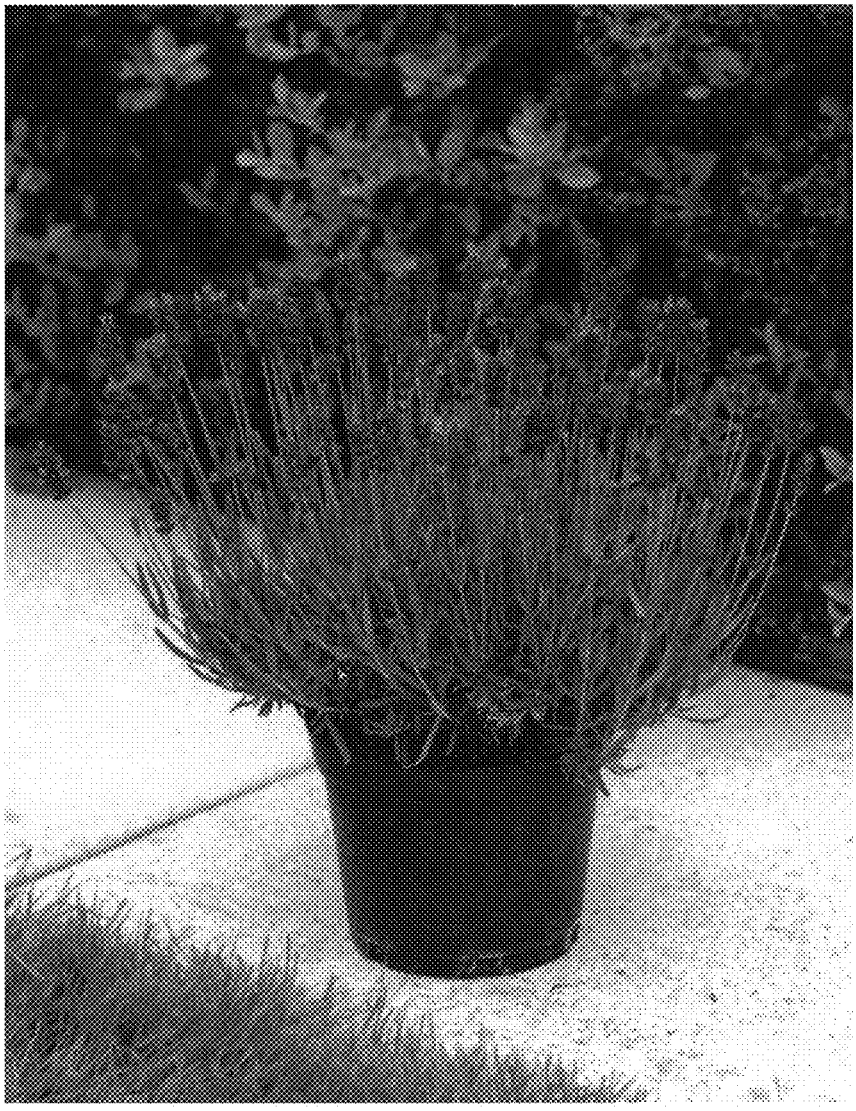
Figure 2:
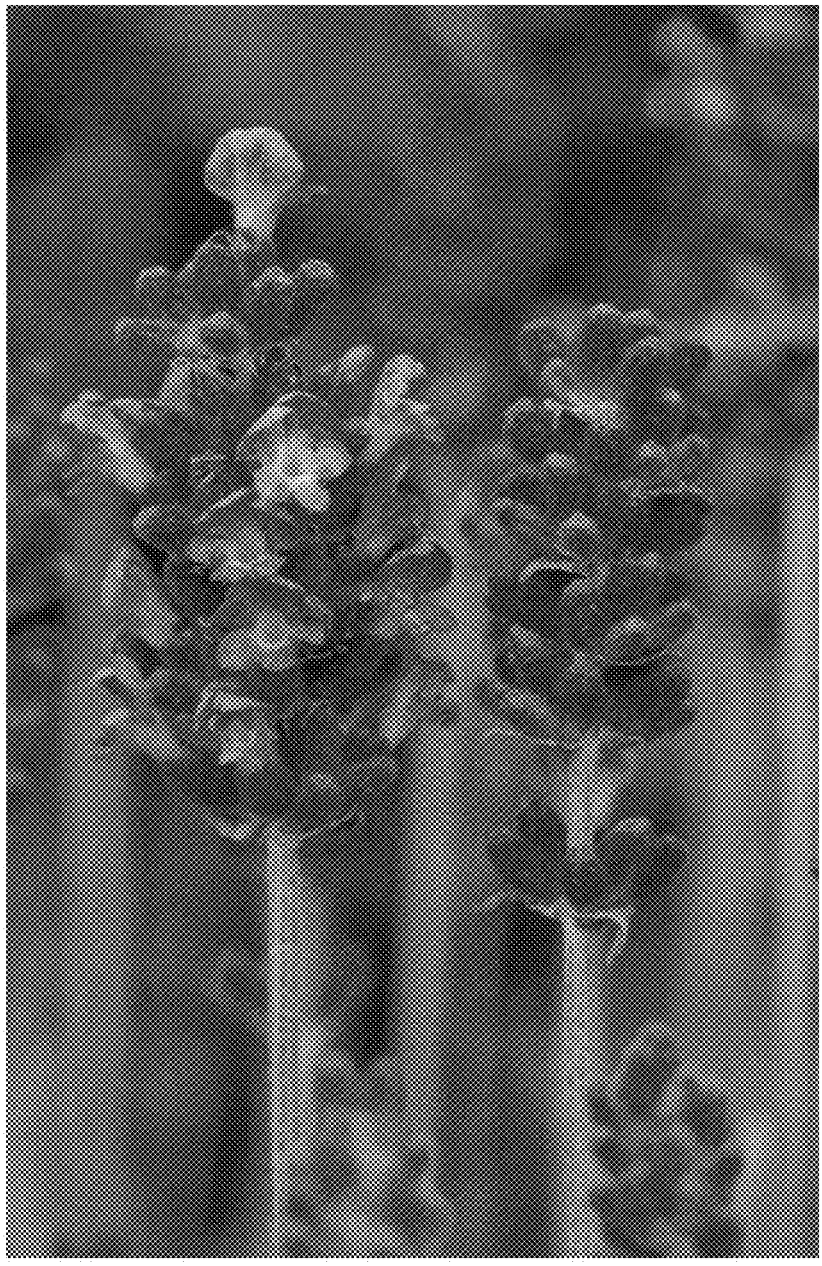
FIG. 2 illustrates a close-up view of a typical inflorescence.
Figure 3:
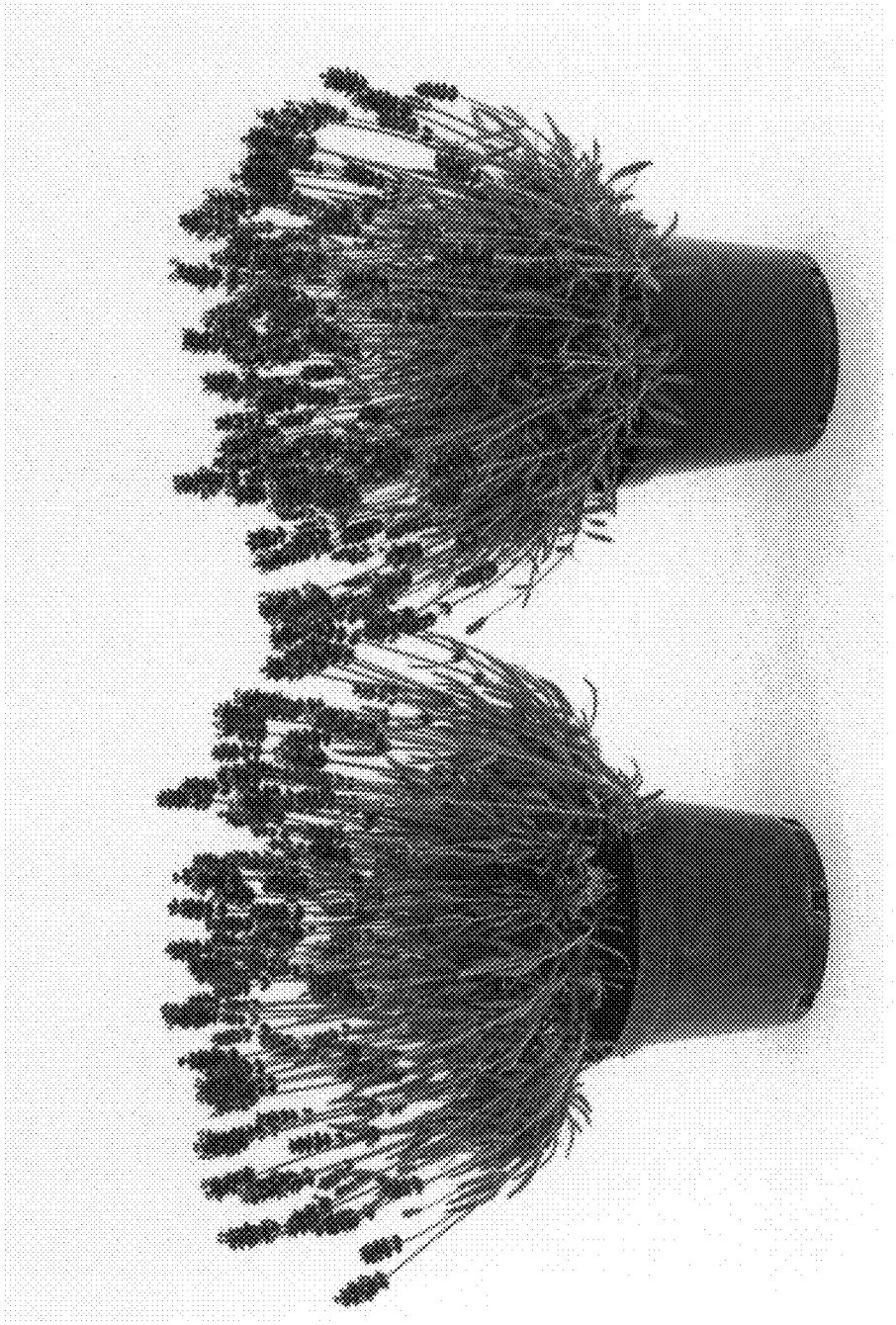
FIG. 3 illustrates a comparison with the well-known commercial variety 'Bee Zee Dark Blue'. 'KERBEEPOWER' is the plant on the left side of the photo, 'Bee Zee Dark Blue' is on the right.
Figure 4:
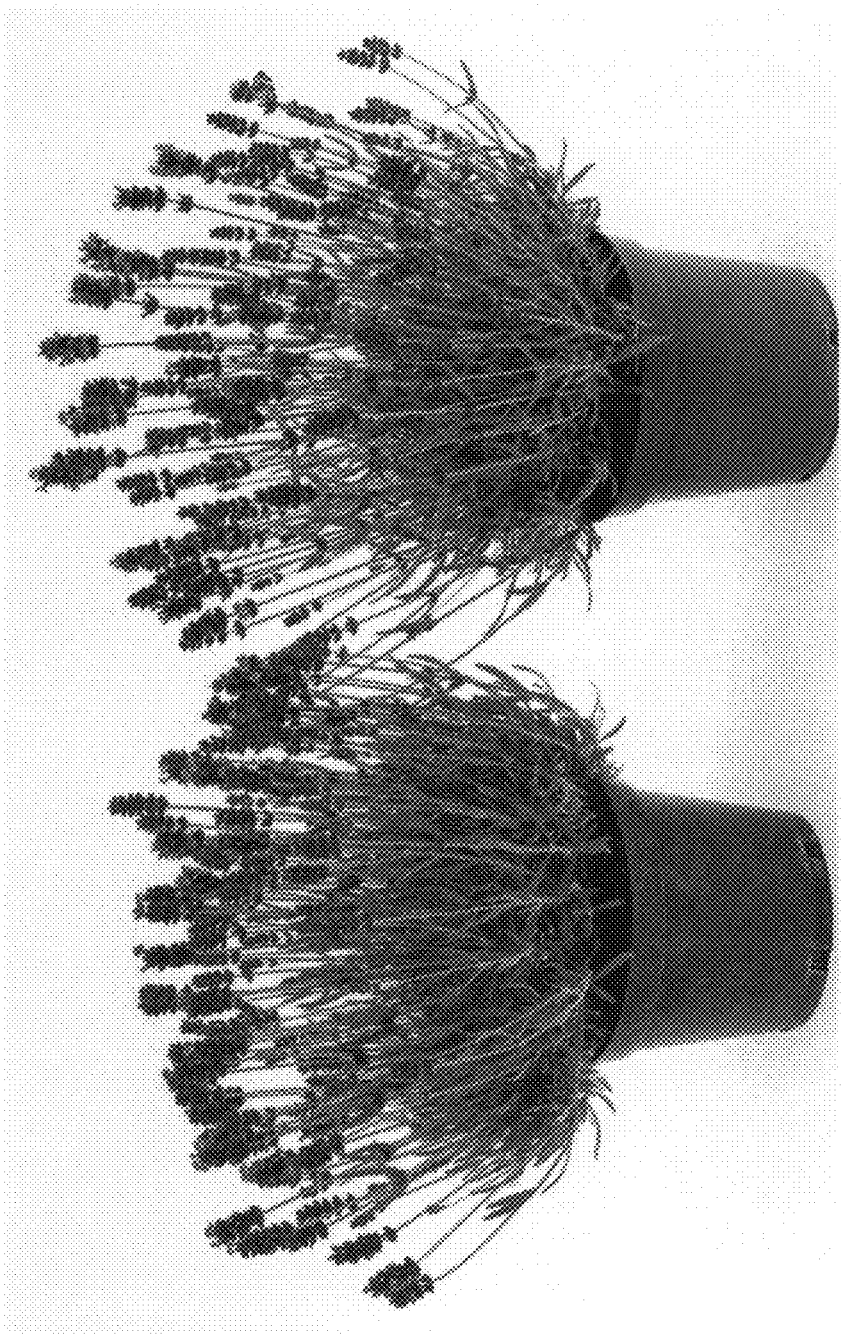
FIG. 4 illustrates a comparison with the commercial variety 'Hidcote'. 'KERBEEPOWER' is the plant on the left side of the photo, 'Hidcote' is on the right.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'KERBEEPOWER' plants grown outdoors in Cambridge, UK. The growing temperature ranged from approximately 0 to 10° C. at night to 10 to 20° C. during the day. Measurements and numerical values represent averages of typical flowering types. No chemical or photoperiodic treatments were given.

Botanical classification: *Lavandula angustifolia* 'KERBEEPOWER'.

Age of the plant described: Approximately 17 weeks, in a 2 liter pot.

PROPAGATION

Time to rooting: About 20 days at approximately 20° C.

Root description: Fine, well branched, becoming woody with age.

PLANT

Growth habit: Upright, slightly spreading. Dense at full flowering.

Height: 13.5 cm to top of plant plane; 28 cm to top of flowers.

Plant spread: 24 cm.

Branching characteristics: Moderate branching.

Length above foliage: Longest lateral branch about 5 to 9 cm above foliage.

Diameter of lateral branches: Approximately 0.2 cm.

Texture of lateral branches: Pubescent.

Internode length: Approximately 1.3 cm.

Strength of stem: Strong.

Color of lateral branches: RHS Yellow-Green 147B.

Number of leaves per lateral branch: 13.

FOLIAGE

Leaf:

- *Arrangement.*—Opposite alternate pairs.
- *Average length.*—3.5 cm.
- *Average width.*—0.4 cm.
- *Shape of blade.*—Narrowly oblanceolate.
- *Apex.*—Acute.
- *Base.*—Cuneate.
- *Attachment.*—Sessile.
- *Margin.*—Entire.
- *Texture of top surface.*—Pubescent.
- *Texture of bottom surface.*—Pubescent.
- *Color.*—Young foliage, upper side: RHS Yellow-Green 147A. Young foliage, under side: RHS Yellow-Green 147B. Mature foliage upper side: RHS Green NN137A. Mature foliage under side: RHS Green NN137B.
- *Venation.*—Type: Very prominent mid-vein, with a network of smaller irregular veins. Venation color upper side: RHS Yellow-Green 146C. Venation color under side: RHS Yellow-Green 146B.

Petiole: Not present.

FLOWER

Bloom period: Naturally blooming June to July.

Inflorescence:

- *Form.*—Small single flower in verticillasters arranged in spikes. Flowers have bracts. Corolla tube has 2 upper lips and 3 lower lips.

Flower spikes:

- *Height.*—3.1 cm.
- *Diameter.*—2.1 cm.
- *Shape.*—Cylindrical.
- *Flowers per spike.*—Average range of 40 to 48 individual flowers per spike, arranged in 5 to 6 whorls, each whorl typically having 8 flowers. Short distance between whorls, about 5 mm.
- *Infertile bracts.*—Interfertile bracts not observed.

Flower bud:

- *Height.*—0.5 cm.
- *Width.*—0.2 cm.
- *Color.*—RHS Violet-Blue 90A.

Individual flower:

- *Corolla.*—Length of upper lobes (2): 0.5 cm.
- *Corolla.*—Length of lower lobes (3): 3 0.3 cm.
- *Corolla.*—Width of upper lobes: 0.4 cm.
- *Corolla.*—Width of lower lobes: 0.3 cm.
- *Corolla tube length.*—About 0.3 cm.
- *Shape of upper lobes.*—2 conjoined lobes.
- *Shape of lower lobes.*—3 smaller lobes, fused about half-length.
- *Apex of upper lobes.*—Blunt and rounded.
- *Apex of lower lobes.*—Mucronate.
- *Texture of corolla.*—Upper surface: Slightly savoyed.
- *Texture of corolla.*—Lower surface: Slightly savoyed.
- *Color when opening.*—Upper surface: RHS Violet-Blue 90B.
- *Color when opening.*—Lower surface: RHS Violet-Blue 90C.
- *Color when fully open.*—RHS Violet N88A/B.
- *Corolla tube color.*—Exterior RHS Violet-Blue 90C. Interior RHS Violet-Blue 90D.

*Calyx arrangement*.—Tubes.
*Calyx width*.—0.6 cm.
*Sepal length*.—0.5 cm.
*Sepal texture*.—Hirsute.
*Sepal color*.—Flower open: RHS Violet N88A, Yellow-Green 145C at base.
*Sepal color*.—Fully open: RHS Violet-Blue N92A.

Inflorescence bracts (3 buds subtend from each bract):
*Bract width*.—0.4 cm.
*Bract height*.—0.4 cm.
*Bract color*.—Near RHS Grey-Brown 199A.

Peduncle:
*Peduncle length*.—8.5 cm.
*Peduncle diameter*.—0.2 cm.
*Aspect*.—Upright.
*Color*.—RHS Greyed-Green 191A.

REPRODUCTIVE ORGANS

Filament length: 0.2 cm.
Anther length: 0.2 cm.
Anther color: RHS Greyed-Orange 175D.
Pollen amount: None present.
Pistil length: 0.5 cm.
Style length: 0.3 cm.
Style color: RHS Green-White 157D.
Stigma color: RHS Greyed-Green 196A.

OTHER CHARACTERISTICS

Fragrance: Strong lavender scent, both flowers and foliage.
Disease resistance: Neither resistance nor susceptibility to diseases or pests has been observed in this variety.
Drought tolerance and cold tolerance: Hardy perennial. Tolerates high temperature to at least 32° C. Tolerates low temperatures to −12° C. While specific drought tolerance has not been observed, once plants are established very little water is necessary to maintain plants.
Fruit/deed production: Fruit and seed production not observed.

What is claimed is:

1. A new and distinct cultivar of *Lavandula* plant named 'KERBEEPOWER' as herein illustrated and described.

* * * * *